(12) United States Patent
Mohn et al.

(10) Patent No.: US 9,082,272 B2
(45) Date of Patent: Jul. 14, 2015

(54) CIRCUIT FOR APPLYING HEAT AND ELECTRICAL STIMULATION

(75) Inventors: Louise Mohn, Oslo (NO); Ole Brix, Bergen (NO); Bard Henriksen, Bergen (NO); Inge Klepsvik, Bergen (NO)

(73) Assignee: Louise Mohn, London (GB)

( * ) Notice: Subject to any disclaimer, the term of this patent is extended or adjusted under 35 U.S.C. 154(b) by 0 days.

(21) Appl. No.: 13/881,575

(22) PCT Filed: Oct. 28, 2011

(86) PCT No.: PCT/EP2011/069047
§ 371 (c)(1),
(2), (4) Date: Nov. 6, 2013

(87) PCT Pub. No.: WO2012/056025
PCT Pub. Date: May 3, 2012

(65) Prior Publication Data
US 2014/0052198 A1    Feb. 20, 2014

(30) Foreign Application Priority Data
Oct. 28, 2011    (EP) .................................... 10189306

(51) Int. Cl.
A61N 1/00    (2006.01)
A61B 5/04    (2006.01)
(Continued)

(52) U.S. Cl.
CPC ... *G08B 5/22* (2013.01); *A61F 7/00* (2013.01); *A61F 7/02* (2013.01); *A61N 1/0456* (2013.01); *A61N 1/0492* (2013.01); *A61N 1/36* (2013.01); *A61N 1/37235* (2013.01); *A61B 19/44* (2013.01); *A61B 2017/00084* (2013.01); *A61F 2007/0058* (2013.01); *A61F 2007/0075* (2013.01); *A61F 2007/0093* (2013.01); *A61F 2007/0096* (2013.01); *A61F 2007/0295* (2013.01); *A61N 1/36021* (2013.01)

(58) Field of Classification Search
CPC ................. A61N 1/36021; A61B 2018/00791
USPC ............................................... 607/3; 600/372
See application file for complete search history.

(56) References Cited

U.S. PATENT DOCUMENTS 3,099,137 A    7/1963    Ewing
3,132,688 A    5/1964    Nowak
(Continued)

FOREIGN PATENT DOCUMENTS

CN    86208439    3/1988
CN    201119003    9/2008
(Continued)

OTHER PUBLICATIONS

International Patent Application No. PCT/EP2011/069047, International Search Report dated May 3, 2012, 4 pages.
(Continued)

*Primary Examiner* — Nicole F Lavert
(74) *Attorney, Agent, or Firm* — Morgan Lewis & Bockius LLP

(57) ABSTRACT

A circuit (51) for applying heat and electrical stimulation comprises a substrate (500). The substrate (500) comprises an electrode (514) for applying electrical stimulation and a heating element (502). At least one of the electrode (514) and the heating element (502) comprises an electrically conducting region patterned on a surface of the substrate (500). The substrate (500) can be flexible.

23 Claims, 5 Drawing Sheets

(51) Int. Cl.

| | |
|---|---|
| *G08B 5/22* | (2006.01) |
| *A61F 7/02* | (2006.01) |
| *A61N 1/04* | (2006.01) |
| *A61N 1/372* | (2006.01) |
| *A61B 19/00* | (2006.01) |
| *A61B 17/00* | (2006.01) |
| *A61F 7/00* | (2006.01) |
| *A61N 1/36* | (2006.01) |

(56) References Cited

U.S. PATENT DOCUMENTS

| | | |
|---|---|---|
| D203,092 S | 11/1965 | Grube |
| 3,249,108 A | 5/1966 | Terman |
| D207,080 S | 2/1967 | McNair |
| 3,556,096 A | 1/1971 | Fuller et al. |
| D243,476 S | 2/1977 | Avery |
| D251,548 S | 4/1979 | Perry |
| D254,726 S | 4/1980 | Hirsch et al. |
| 4,353,372 A | 10/1982 | Ayer |
| 4,364,378 A | 12/1982 | Seuss et al. |
| 4,570,640 A | 2/1986 | Barsa |
| D288,179 S | 2/1987 | Sekido |
| 4,895,154 A | 1/1990 | Bartelt et al. |
| 4,919,139 A | 4/1990 | Brodard |
| 4,990,077 A | 2/1991 | Morita |
| D319,121 S | 8/1991 | Muller |
| 5,092,344 A | 3/1992 | Lee |
| 5,097,828 A | 3/1992 | Deutsch |
| 5,172,949 A | 12/1992 | Nagai et al. |
| 5,183,039 A | 2/1993 | Sarian et al. |
| D345,706 S | 4/1994 | Martell |
| 5,300,105 A | 4/1994 | Owens |
| 5,314,456 A | 5/1994 | Cohen |
| 5,336,255 A | 8/1994 | Kanare et al. |
| 5,412,181 A | 5/1995 | Giamati |
| D359,805 S | 6/1995 | Mikler et al. |
| D359,807 S | 6/1995 | Mikler et al. |
| D371,517 S | 7/1996 | Narayanan |
| D371,605 S | 7/1996 | Wong et al. |
| 5,601,618 A | 2/1997 | James |
| 5,785,716 A | 7/1998 | Bayron et al. |
| 5,891,187 A | 4/1999 | Winthrop et al. |
| 5,961,869 A | 10/1999 | Irgens |
| D419,082 S | 1/2000 | Wensley et al. |
| 6,021,348 A | 2/2000 | James |
| D426,924 S | 6/2000 | Joiner et al. |
| 6,078,549 A | 6/2000 | Wyatt et al. |
| 6,125,636 A | 10/2000 | Taylor et al. |
| 6,261,595 B1 | 7/2001 | Stanley et al. |
| D447,071 S | 8/2001 | Akers, III et al. |
| 6,302,901 B1 | 10/2001 | Lu |
| 6,325,536 B1 | 12/2001 | Renken et al. |
| 6,372,951 B1 | 4/2002 | Ter-Ovanesyan et al. |
| D456,907 S | 5/2002 | Sanfillippo |
| D476,160 S | 6/2003 | Choi |
| D477,540 S | 7/2003 | Chen |
| 6,603,995 B1 | 8/2003 | Carter |
| D481,963 S | 11/2003 | Onuma et al. |
| 6,840,955 B2 | 1/2005 | Ein |
| 6,893,453 B2 | 5/2005 | Agarwal et al. |
| D511,384 S | 11/2005 | Masuda |
| D540,498 S | 4/2007 | Tobias |
| D541,494 S | 4/2007 | Tsen |
| D541,500 S | 4/2007 | Leung |
| D545,439 S | 6/2007 | Draudt et al. |
| D547,067 S | 7/2007 | Choi |
| 7,257,448 B2 | 8/2007 | Crowe et al. |
| D553,248 S | 10/2007 | Nguyen |
| D561,958 S | 2/2008 | Hahn |
| D569,523 S | 5/2008 | Hsieh |
| D574,568 S | 8/2008 | Lee |
| D576,363 S | 9/2008 | Reiner |
| D585,993 S | 2/2009 | Kousuge |
| 7,490,422 B1 | 2/2009 | Chen |
| D589,663 S | 3/2009 | Massip et al. |
| D590,063 S | 4/2009 | Garthoff et al. |
| 7,516,565 B1 | 4/2009 | Tsen |
| D592,365 S | 5/2009 | Massip et al. |
| D595,461 S | 6/2009 | Massip et al. |
| D595,964 S | 7/2009 | Choi |
| D601,806 S | 10/2009 | Choi |
| D601,807 S | 10/2009 | Choi |
| D606,947 S | 12/2009 | Caprio |
| D607,947 S | 1/2010 | Antonopoulos et al. |
| D622,401 S | 8/2010 | Suzuki |
| D622,457 S | 8/2010 | Choi |
| 7,787,946 B2 | 8/2010 | Stahmann et al. |
| D633,625 S | 3/2011 | Maderazzo |
| D642,564 S | 8/2011 | Busri et al. |
| D653,761 S | 2/2012 | Lytle |
| 8,121,679 B2 | 2/2012 | Fruitman |
| D667,557 S | 9/2012 | Boudier |
| D671,649 S | 11/2012 | McCormack |
| D672,668 S | 12/2012 | Gibb et al. |
| D675,738 S | 2/2013 | Baumer et al. |
| D678,532 S | 3/2013 | Powers et al. |
| D681,486 S | 5/2013 | Willuweit |
| D681,827 S | 5/2013 | Shinohara et al. |
| D681,828 S | 5/2013 | Shinohara et al. |
| D682,433 S | 5/2013 | Shinohara et al. |
| D685,100 S | 6/2013 | Shinohara et al. |
| D689,614 S | 9/2013 | Browne et al. |
| 2002/0088788 A1 | 7/2002 | West |
| 2003/0120174 A1 | 6/2003 | Ippolito et al. |
| 2004/0045955 A1 | 3/2004 | Rock et al. |
| 2004/0075528 A1 | 4/2004 | Carbin et al. |
| 2004/0186535 A1 | 9/2004 | Knowlton |
| 2004/0260212 A1 | 12/2004 | Cho |
| 2005/0045623 A1 | 3/2005 | Schenck et al. |
| 2005/0060012 A1 | 3/2005 | Voorhees et al. |
| 2005/0116384 A1 | 6/2005 | Hyuga et al. |
| 2005/0256550 A1 | 11/2005 | Gilkerson et al. |
| 2006/0030759 A1 | 2/2006 | Weiner et al. |
| 2006/0052852 A1 | 3/2006 | Wyatt et al. |
| 2006/0064037 A1 | 3/2006 | Shalon et al. |
| 2006/0122673 A1 | 6/2006 | Callister et al. |
| 2006/0142816 A1 | 6/2006 | Fruitman et al. |
| 2006/0241720 A1 | 10/2006 | Woods et al. |
| 2007/0016099 A1 | 1/2007 | Chin et al. |
| 2007/0129760 A1 | 6/2007 | Demarais et al. |
| 2007/0179575 A1 | 8/2007 | Esch et al. |
| 2007/0180902 A1 | 8/2007 | Sherwood et al. |
| 2008/0018891 A1 | 1/2008 | Hell et al. |
| 2008/0021520 A1 | 1/2008 | Dietrich |
| 2008/0058685 A1 | 3/2008 | Hsieh |
| 2008/0097557 A1* | 4/2008 | Eggers et al. ............... 607/99 |
| 2008/0140165 A1 | 6/2008 | Cohen et al. |
| 2008/0183229 A1 | 7/2008 | Neumiller et al. |
| 2008/0188911 A1 | 8/2008 | Chao |
| 2008/0221398 A1 | 9/2008 | Ronchi et al. |
| 2008/0221473 A1 | 9/2008 | Calancie et al. |
| 2008/0269652 A1 | 10/2008 | Reiner |
| 2008/0269843 A1 | 10/2008 | Gerber et al. |
| 2008/0300534 A1 | 12/2008 | Blomquist |
| 2008/0313816 A1 | 12/2008 | Bohm |
| 2009/0004557 A1 | 1/2009 | Lasarov |
| 2009/0020521 A1 | 1/2009 | Blaszczykiewicz et al. |
| 2009/0078043 A1 | 3/2009 | Tsuda et al. |
| 2009/0149731 A1 | 6/2009 | Selvitelli et al. |
| 2009/0163984 A1 | 6/2009 | Robinson et al. |
| 2010/0228304 A1* | 9/2010 | Kriksunov et al. ............ 607/3 |
| 2010/0256694 A1 | 10/2010 | Barker |
| 2010/0305632 A1 | 12/2010 | Maskara et al. |
| 2011/0054580 A1 | 3/2011 | Desai et al. |
| 2011/0093052 A1 | 4/2011 | Anderson et al. |
| 2011/0125204 A1 | 5/2011 | Louise |
| 2011/0205141 A1 | 8/2011 | Hong et al. |
| 2011/0245903 A1 | 10/2011 | Schulte et al. |

FOREIGN PATENT DOCUMENTS

| | | |
|---|---|---|
| CN | 201371557 | 12/2009 |
| DE | 10212794 | 6/2003 |

(56) References Cited

FOREIGN PATENT DOCUMENTS

| | | |
|---|---|---|
| DE | 10-2005-019868 | 11/2006 |
| EP | 0165049 | 12/1985 |
| EP | 1321164 | 6/2003 |
| EP | 1357774 | 10/2003 |
| EP | 1829580 | 9/2007 |
| EP | 1977710 | 10/2008 |
| ES | 1045721 | 10/2000 |
| GB | 2424613 | 10/2006 |
| JP | S55-118845 | 9/1980 |
| JP | H02-41221 | 2/1990 |
| JP | 2005-053127 | 3/2005 |
| JP | 2007-313102 | 12/2007 |
| KR | 10-0915320 | 9/2009 |
| WO | WO 95/10323 | 4/1995 |
| WO | WO 96/11098 | 4/1996 |
| WO | WO 97/18854 | 5/1997 |
| WO | WO 2006/081883 | 8/2006 |
| WO | WO 2006/125092 | 11/2006 |
| WO | WO 2007/107831 | 9/2007 |
| WO | WO 2008/137319 | 11/2008 |
| WO | WO 2009/006517 | 1/2009 |
| WO | WO 2011/064527 | 6/2011 |
| WO | WO 2011/075480 | 6/2011 |

OTHER PUBLICATIONS

International Patent Application No. PCT/EP2011/069049, International Search Report, dated Feb. 1, 2012, 5 pages.
International Patent Application No. PCT/EP2011/069050, International Search Report, dated Feb. 2, 2012, 5 pages.
International Patent Application No. PCT/EP2013/056064, International Search Report, dated Jun. 26, 2013, 3 pages.
International Patent Application No. PCT/EP2013/056059, International Search Report, dated Aug. 27, 2013, 5 pages.
"Sunice Hot and Cold Therapy" win-health.com, Oct. 2010, http://www.win-health.com/sunice-hot-cold-therapy.html, 3 pages.
"Professional Portable Ultrasound Machine", EZUltrasound, Jul. 3, 2009, http://www.ezultrasound.com/us1000-portable-home-ultrasound-therapy-machine.aspx, 5 pages.
"Infared Light Therapy Polychromatic LED Therapy Device Model 900", Healiohealth.com, 2010, www.http://healiohealth.com/products/index/2026, 1 page.
"Hammacher Heat and Cold Therapy Massager", itclips.net, Nov. 22, 2011, http://www.itclips.net/2011/11/22/hammacher-heat-and-cold-therapy-massager/, 1 page.
"Jade Product DV12V 3 Balls Heating Therapy Massager", Alibaba.com, Apr. 12, 2010, http://www/alibaba.com/product-gs-1256700104/Jade_Product_DV12V_3_balls_Jade/showimage.html, 1 page.

* cited by examiner

CIRCUIT FOR APPLYING HEAT AND ELECTRICAL STIMULATION

CROSS-REFERENCE TO RELATED APPLICATION

This application is a U.S. National Phase Application under 35 U.S.C. 371 claiming priority to International Application No. PCT/EP2011/069047 filed Oct. 28, 2011, which claims priority to European Patent Application No. 10189306.3 filed Oct. 28, 2010, wherein the entire contents of each application are incorporated herein by reference in their entireties.

FIELD OF THE INVENTION

The present invention relates to a circuit for applying heat and electrical stimulation to a human or animal body.

BACKGROUND OF THE INVENTION

For a variety of therapeutic applications, several treatment modalities are currently known in the art including electrical stimulation, heat therapy and thermostimulation.

Electrical stimulation involves the application of an electrical current to a single muscle or a group of muscles through one or more stimulation pads that are temporarily attached to the skin. The resulting muscle contraction can produce a variety of effects from strengthening injured muscles and reducing oedema to relieving pain and promoting healing. The pads are usually quite small and typically powered with a battery. This results in the application of a small amount of power and a low treatment depth of the resulting electric field. The shallow depth of the electric field generated by conventional electrical stimulation systems limits performance and patient benefit. Some systems have attempted to address this limitation by applying more current, often from a line or mains supply source. However, the small size of conventional electrical stimulation pads is such that on the application of larger amounts of power, i.e. the use of higher currents, patients often report the experience of pain or discomfort.

Heat therapy involves the application of heat to the body. Heat therapy is very useful as it has a number of effects such as relaxation of muscle spasm and increased blood flow that promotes healing. However, combination therapy, i.e. the synergistic use of other modalities such as massage, ultrasound and/or electrical stimulation has been found to be more effective than heat therapy alone.

Thermostimulation is one such combination therapy that involves the use of heat therapy and electrical stimulation simultaneously. With thermostimulation, the healing benefits of heat are provided along with the strengthening, toning, pain relieving and healing benefits of electrical stimulation. Moreover, the application of heat has been found effective in that it allows the patient to tolerate higher currents. This yields higher electric field strengths, greater depths of penetration and, therefore, more positive results than could be achieved with electrical stimulation without heat. Thermostimulation can be performed using pads that are temporarily attached to the skin.

Conventional pads for thermostimulation are small, hard and die cut with sharp flat edges. The rectangular shape of such pads does not conform to the natural shape of muscle tissue. Moreover, conventional thermostimulation pads are generally inflexible and yield to breakage of the heating element if bent or folded too frequently.

The applicant's earlier patent application, WO 2011/064527, describes a solution to the problems of conventional pads for thermostimulation. WO 2011/064527 describes a thermostimulation pad having two elongate substantially parallel electrodes for electrical stimulation, each preferably moulded from carbon loaded silicone. The electrodes are then over-moulded, to hold the electrodes in position relative to one another, thereby providing a single moulded assembly. A heating element is positioned on the moulded assembly and held in place with a layer of silicone. However, whilst the resulting pad has improved flexibility, the inventors have identified a need for a thermostimulation pad that is simpler to manufacture.

SUMMARY OF THE INVENTION

An aspect of the invention provides a circuit for applying heat and electrical stimulation, the circuit comprising a substrate, the substrate comprising an electrode for applying electrical stimulation and a heating element, wherein at least one of the electrode and the heating element comprises an electrically conducting region patterned on a surface of the substrate. This results in a circuit that is compact and simple to manufacture.

Preferably, the substrate comprises a first surface and a second surface, the first surface being oppositely oriented to the second surface, wherein the electrode is provided on the first surface and the heating element is provided on the second surface. Providing the electrode and heating element on opposite surfaces of a single substrate results in a circuit that is compact.

Preferably, the position, on the second surface, of at least a portion of the heating element corresponds to the position, on the first surface, of the electrode, such that the at least a portion of the heating element is operable to heat the electrode. This allows heat and electrical stimulation to be applied simultaneously at the same point, which can enhance the therapeutic effect of thermostimulation. Preferably, the heating element comprises one or more resistors, wherein the position of the resistors on the second surface corresponds to the position, on the first surface, of the electrode.

Preferably, the heating element comprises one or more resistors mounted on a surface of the substrate. Mounting resistors on the surface of the substrate, using surface-mount technology, allows the circuit to be easily mass-produced.

Preferably, the heating element comprises a plurality of resistors, and wherein the resistors are positioned so as to produce a predetermined heat distribution when a current is applied to the heating element. Preferably, the heating element comprises a plurality of resistors, each resistor having a respective resistance value, wherein the resistance values of the plurality of resistors are chosen so as to produce a predetermined heat distribution when a current is applied to the heating element. The therapeutic effect of thermostimulation can be enhanced by optimising the heat distribution produced by the heating element.

Preferably the resistors are electrically connected to an electrically conducting region patterned on a surface of the substrate that forms part of the heating element. Preferably, the electrically conducting region that forms part of the heating element is shaped such that its resistance is negligible relative to the resistance of each resistor. This simplifies the process of designing a heating element having a particular heat distribution, by allowing the heat distribution to be primarily determined by the positions and resistance values of the resistors.

Preferably, both the electrode and the heating element comprise an electrically conducting region patterned on a surface of the substrate. This avoids the need for external components or mouldings to hold the electrode and heating electrodes in position relative to each other.

Preferably, the circuit further comprises a temperature sensor mounted on a surface of the substrate. The temperature sensor is operable to measure the temperature of the circuit. Thus, the temperature of the thermostimulation pad comprising the circuit can be regulated to prevent harm to the user. Preferably, the temperature sensor is mounted on a surface of the substrate. Mounting the temperature sensor on a surface of the substrate, using surface-mount technology, allows the circuit to be easily mass-produced.

Preferably, the heating element comprises one or more resistors mounted on the same surface of the substrate as the temperature sensor. This allows the temperature sensor to measure the temperature on the surface where the heat is produced.

Preferably, the circuit comprises a further electrode for applying electrical stimulation, wherein the temperature sensor is positioned between the electrode and the further electrode. This allows the temperature sensor to measure the temperature close to where the electrical stimulation is applied.

Preferably, the substrate is flexible. This allows the circuit to be flexible and so to conform to the contours of the body.

A further aspect of the invention provides a circuit for applying heat and electrical stimulation, the circuit comprising an electrode for applying electrical stimulation and a heating element, wherein the circuit is formed on a flexible substrate. This allows the circuit to be flexible and so to conform to the contours of the body.

Preferably, the flexible substrate comprises a first surface and a second surface, the first surface being oppositely oriented to the second surface, wherein the electrode is provided on the first surface and the heating element is provided on the second surface. Providing the electrode and heating element on opposite surfaces of a single flexible substrate results in a circuit that is compact.

Preferably, the position, on the second surface, of at least a portion of the heating element corresponds to the position, on the first surface, of the electrode, such that the at least a portion of the heating element is operable to heat the electrode. This allows heat and electrical stimulation to be applied simultaneously at the same point, which can enhance the therapeutic effect of thermostimulation. Preferably, the heating element comprises one or more resistors, wherein the position of the resistors on the second surface corresponds to the position, on the first surface, of the electrode.

Preferably, the heating element comprises one or more resistors mounted on a surface of the flexible substrate. Mounting resistors on the surface of the flexible substrate, using surface-mount technology, allows the circuit to be easily mass-produced.

Preferably, the heating element comprises a plurality of resistors, and wherein the resistors are positioned so as to produce a predetermined heat distribution when a current is applied to the heating element. Preferably, the heating element comprises a plurality of resistors, each resistor having a respective resistance value, wherein the resistance values of the plurality of resistors are chosen so as to produce a predetermined heat distribution when a current is applied to the heating element. The therapeutic effect of thermostimulation can be enhanced by optimising the heat distribution produced by the heating element.

Preferably the resistors are electrically connected to an electrically conducting region that forms part of the heating element, wherein the electrically conducting region is shaped such that its resistance is negligible relative to the resistance of each resistor. This simplifies the process of designing a heating element having a particular heat distribution, by allowing the heat distribution to be primarily determined by the positions and resistance values of the resistors.

Preferably, the circuit further comprises a temperature sensor mounted on a surface of the flexible substrate. The temperature sensor is operable to measure the temperature of the circuit. Thus, the temperature of the thermostimulation pad comprising the circuit can be regulated to prevent harm to the user. Preferably, the temperature sensor is mounted on a surface of the flexible substrate. Mounting the temperature sensor on surface of the flexible substrate, using surface-mount technology, allows the circuit to be easily mass-produced.

Preferably, the heating element comprises one or more resistors mounted on the same surface of the flexible substrate as the temperature sensor. This allows the temperature sensor to measure the temperature on the surface where the heat is produced.

Preferably, the circuit comprises a further electrode for applying electrical stimulation, wherein the temperature sensor is positioned between the electrode and the further electrode. This allows the temperature sensor to measure the temperature close to where the electrical stimulation is applied.

A further aspect of the invention provides an apparatus substantially as described herein and/or as illustrated in any of the accompanying drawings.

BRIEF DESCRIPTION OF THE DRAWINGS

Preferred features of the invention will now be described, purely by way of example, with reference to the accompanying drawings, wherein like elements are indicated using like reference signs, and in which.

DETAILED DESCRIPTION

Figure 1:
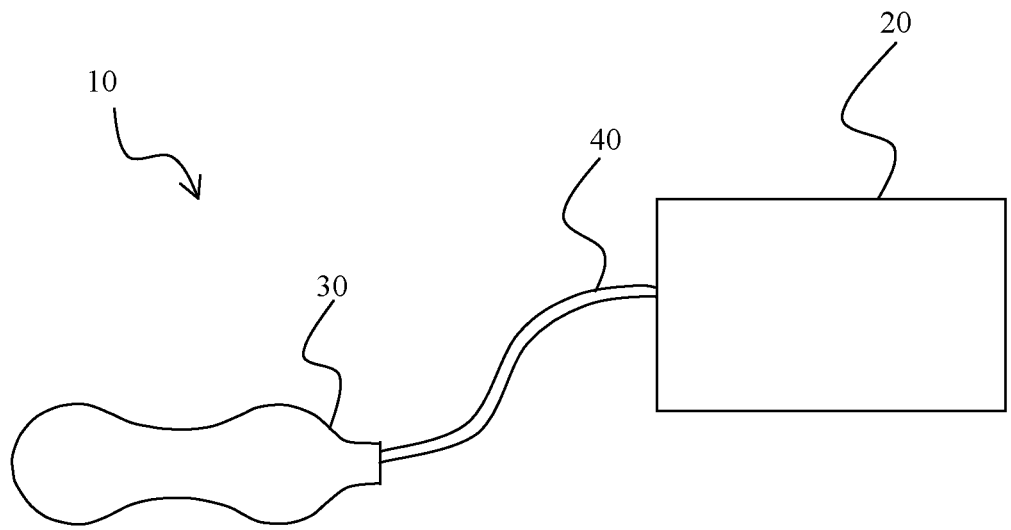
FIG. 1 is a schematic diagram of a thermostimulation system.

FIG. 1 shows a thermostimulation system 10, which includes a thermostimulation console 20 with a thermostimulation pad assembly 30 electrically coupled thereto. The pad assembly 30 is detachably connected to the console by a cable 40. The console 20 is operable to provide a heating current and an electrical stimulation current to the pad assembly 30 via the cable 40. The pad assembly 30 uses the heating current to apply heat to a human or animal body. The pad assembly 30 uses the electrical stimulation current to apply electrical stimulation to the human or animal body. Heat and electrical stimulation can be applied to the body simultaneously or independently of one another. The console 20 could be a conventional thermostimulation console provided by Ross Estetica of Barcelona, Spain. Alternatively, the console 20 could be the novel thermostimulation console described in GB patent application No. 1101498.2, filed on 28 Jan. 2011, the entire contents of which are incorporated by reference herein. Other suitable consoles could also be used with the circuit described herein.

Figure 2:
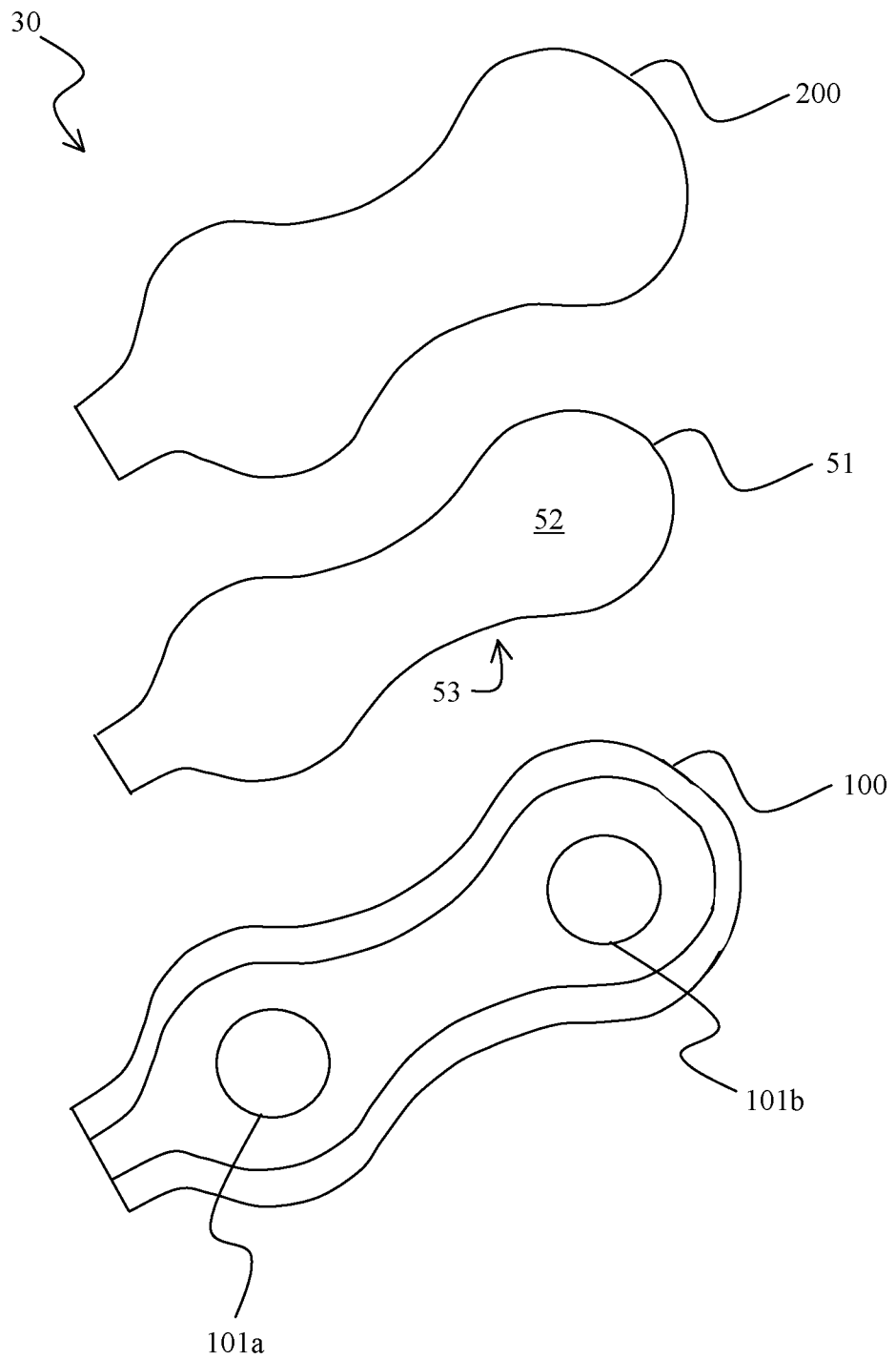
FIG. 2 is an exploded view of a pad assembly for use with the thermostimulation system of FIG. 1.

The pad assembly 30 comprises a circuit enclosed within a protective casing. FIG. 2 shows an exploded view of the pad assembly 30. The circuit 51 fits into a casing body 100. The casing body 100 may be moulded from a plastics material. The casing body 100 comprises areas 101a, 101b of conducting material 101. The areas of conducting material 101 may comprise a polymer mixed with graphite. When fitted, a first surface 53 of the circuit 51 faces towards the casing body 100 and is aligned so each electrode 514a, 514b (shown in FIG. 4) is in electrical contact with a respective conducting area 101a, 101b. A cover 200 is provided on top of the casing body 100, thereby enclosing the circuit 51. The casing body 100 and cover 200 protect the circuit 51 against the ingress of water, which could cause the circuit 51 to malfunction. In use, the pad assembly 30 is placed on the body of a user. The conducting areas 101 conduct an electrical current from the electrodes 514 to the body of the user.

Figure 3:
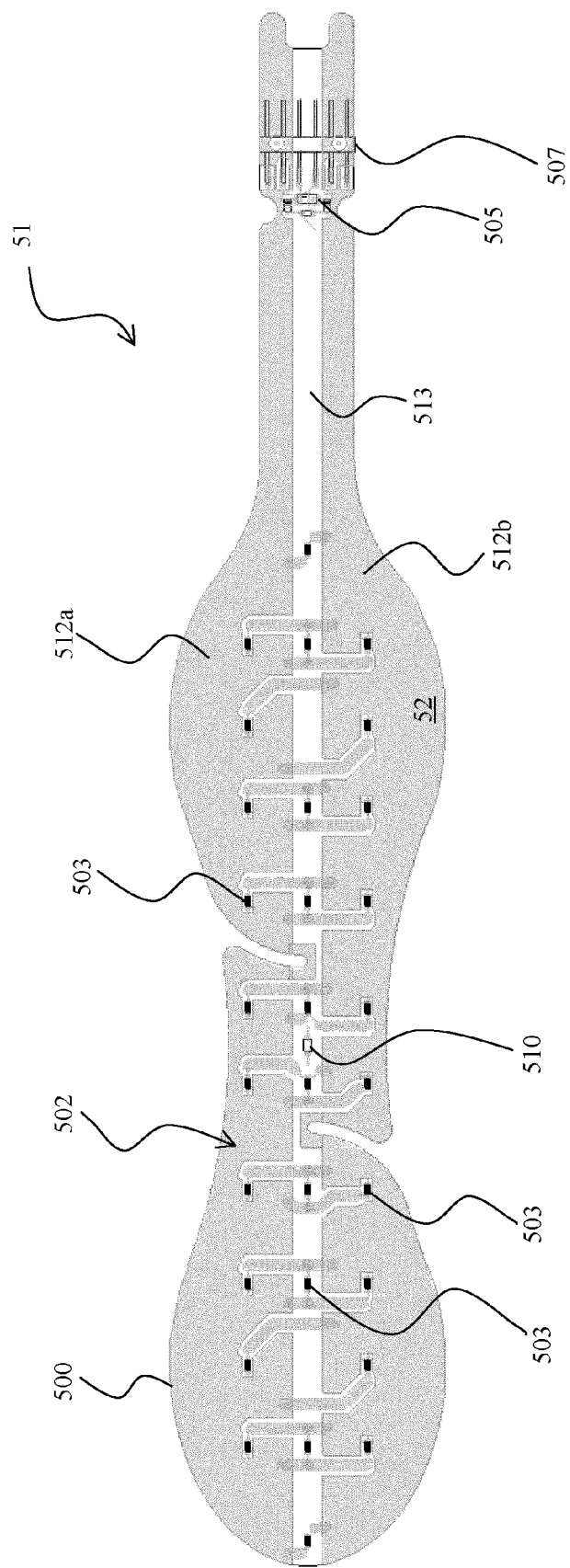
FIG. 3 is a top plan view of a circuit for use with the pad assembly of FIG. 2.
Figure 4:
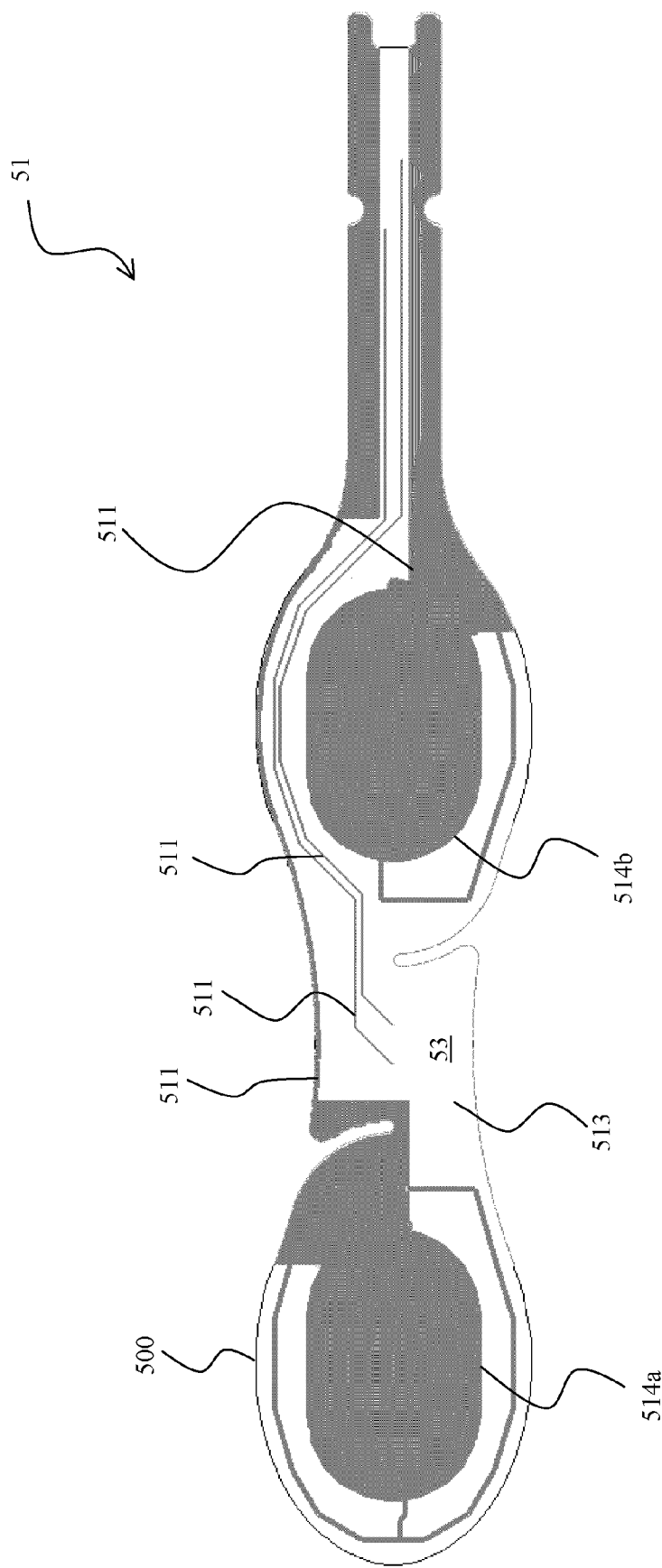
FIG. 4 is a bottom plan view of the circuit shown in FIG. 3.

FIG. 3 is a top plan view of the circuit 51 of the pad assembly 30 shown in FIGS. 1 and 2. FIG. 4 is a bottom plan view of the circuit 51. As shown in FIG. 3 and FIG. 4, the circuit 51 comprises a substrate 500. The substrate 500 has a first surface 53 (shown in FIG. 4) and a second surface 52 (shown in FIG. 3), wherein the first surface 53 has an opposite orientation to the second surface 52. The circuit 51 further comprises a heating element 502 and one or more electrodes 514. The circuit 51 can further comprise electronic components including a temperature sensor 510, a visual indicator 505 and a connector 507.

Electrical conductors 511, 512 are patterned on each surface 52, 53 of the substrate 500 to form electrical connections between the components of the circuit 51. The conductors are illustrated by the grey shaded areas in FIGS. 3 and 4. The conductors on the first surface 53 are denoted by reference numeral 511 in FIG. 4, whilst the conductors on the second surface 52 are denoted by reference numeral 512 in FIG. 3. One or more electrodes 514 are also patterned on the first surface 53 of the substrate 500. The electrodes 514 are also illustrated by grey shaded areas in FIG. 4, since the electrodes 514 are preferably formed from the same electrically conducting material as the conductors 511. Insulating regions that do not comprise a conductor are illustrated in FIGS. 3 and 4 by the unshaded areas denoted by reference numeral 513.

As used herein, the term "patterned" is preferably understood to describe the result of a process whereby an electrically conducting region having a predefined shape is formed upon a surface of the substrate 500. The conductors 511, 512 and electrodes 514 can be patterned on the substrate 500 using any suitable patterning process. One example of a suitable patterning process is etching. In an etching process, a thin conducting layer, such as a layer of copper, is initially bonded to substantially the whole area of a surface 52, 53 of the substrate 500. Part of the conducting layer is then removed, such that the remainder of the conducting layer forms one or more conductors 511, 512 or electrodes 514, each having a predefined shape. Since etching causes part of the conducting layer to be removed, it is said to be a subtractive process. Alternatively or additionally, an additive process can be used, whereby one or more conductors 511, 512 or electrodes 514 having a predefined shape are deposited onto a surface 52, 53 of the substrate 500. An example of an additive patterning process involves inkjet printing of an electrically conductive material onto a surface 52, 53 of the substrate 500. Suitable patterning processes are known to those skilled in the art of printed circuit board design and need not be described in further detail. Preferably the conductors 511, 512 comprise metal. Preferably the metal is copper. Copper is preferable as it has a low resistance and so negligible heat is dissipated in the copper when a current is applied to the conductors 512.

The electronic components 502, 505, 507, 510, conductors 511, 512 and electrodes 514 are provided on both surfaces 52, 53 of the substrate 500. The electrodes 514 are formed on the first surface 53, whilst the heating element 502 is formed on the second surface 52. In use, the heating element 502 faces away from the skin of the user and the electrodes 514 face towards the skin. The temperature sensor 510, visual indicator 505 and connector 507 are also preferably provided on the second surface 52. Since electronic components 502, 505, 507, 510, conductors 511, 512 and electrodes 514 are provided on both surfaces of the substrate 500, the substrate 500 should have electrically insulating properties in order to prevent unwanted electrical conduction between components and conductors on different surfaces.

Figure 5:
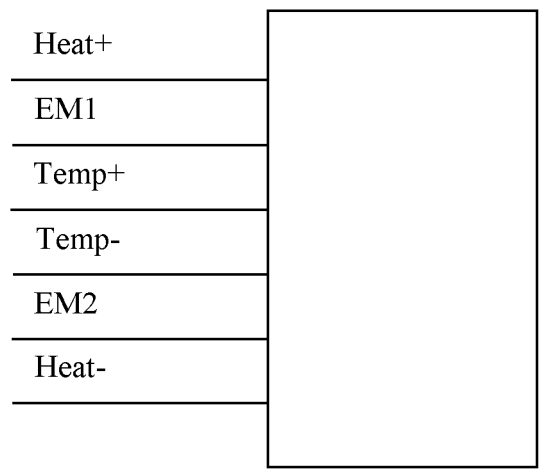
FIG. 5 is a schematic diagram of a connector for the circuit shown in FIG. 3.

The circuit 51 comprises a connector 507 to allow the circuit to be electrically connected to the cable 40 (shown in FIG. 1) and thereby connected to the console 20 (also shown in FIG. 1). The connector 507 is preferably provided on the second surface 52. The connector 507 is preferably a surface-mount connector. The connector 507 comprises connection pins, which can be connected to a corresponding connector on the cable 40. In an example, the connector 507 comprises six connection pins, as illustrated in FIG. 5. The pins labelled 'Heat+' and 'Heat−' are connected to the heating element 502. The pins labelled 'Temp+' and 'Temp−' are connected to the temperature sensor 510. The pins labelled 'EM1' and 'EM2' are connected to the electrodes 514.

The heating element 502 preferably comprises a plurality of resistors 503 and one or more conductors 512. The resistors 503 are distributed across the second surface 52 of the substrate 500. For the sake of clarity, only three resistors 503 are labelled in FIG. 3; however, it can be seen that the circuit comprises many more resistors, each of which is illustrated as a small black rectangle in FIG. 3. The resistors 503 are electrically connected to each other by the conductors 512. In the example illustrated in FIG. 3, conductor 512a is connected to the 'Heat−' pin of the connector 507 such that, in use, the conductor 512a operates as a negative voltage supply rail. Similarly, conductor 512b is connected to the 'Heat+' pin of the connector 507 such that, in use, the conductor 512b operates as a positive voltage supply rail.

Preferably the resistors 503 are surface-mount resistors, which are attached to the substrate 500 using surface-mount technology, which is known to those skilled in the art. Surface-mount technology simplifies the process of manufacturing the circuit 51. Furthermore, by constructing the heating element 502 from a plurality of surface-mount resistors 503 that are connected by conductors 512 patterned on the surface of the substrate 500, the heating element 502 can be easily redesigned to produce a particular heat distribution. The process by which the heating element 502 is designed to produce a predetermined heat distribution is described in more detail below.

When a voltage is applied across the resistors 503, power is dissipated as heat. The positive and negative supply voltages for the heating current are supplied by the pins labelled 'Heat+' and 'Heat−' respectively in the connector 507. The resistors 503 are soldered to the conductors 512, and are thereby electrically connected to the connector 507. The power dissipated by each resistor 503 is defined as:

$$P = I^2 R \qquad (1)$$

where P is the power dissipated (measured in watts), I is the current through the resistor (measured in amperes), and R is the resistance of the resistor (measured in ohms).

Figure 6:
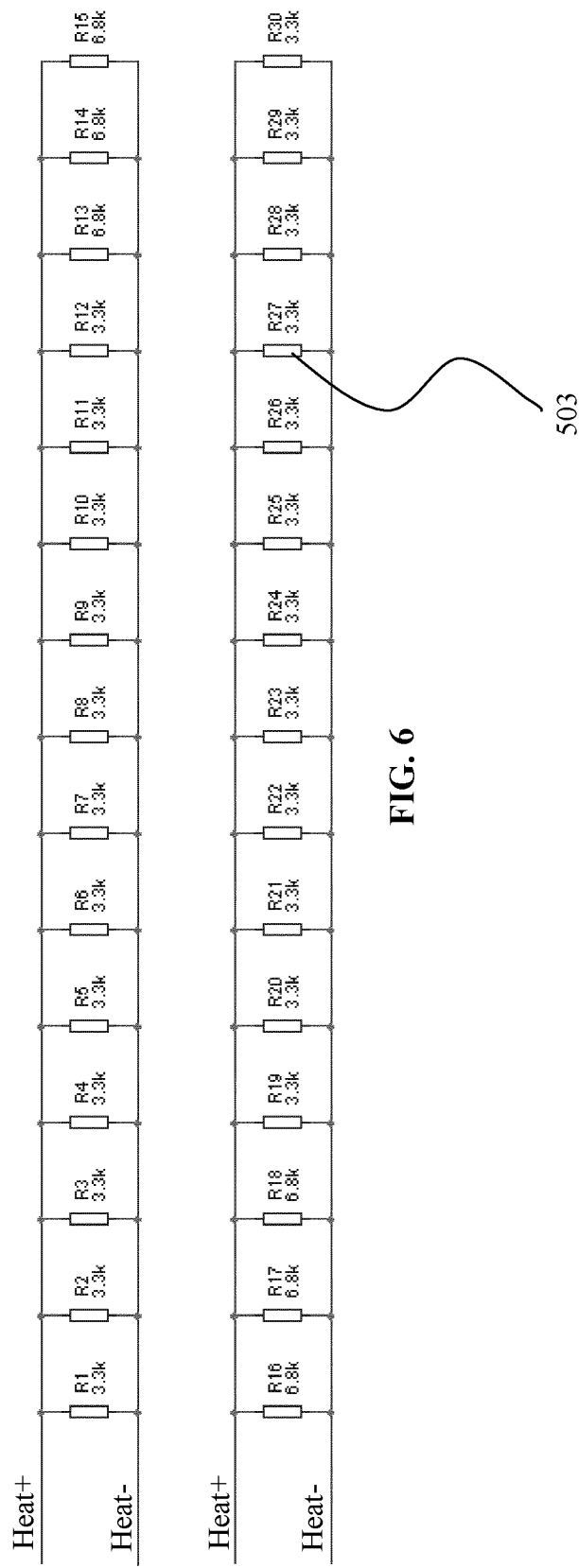
FIG. 6 is a circuit diagram of a heating element for the circuit shown in FIG. 3.

In an example, thirty resistors 503 are distributed over the area of the second surface 52. FIG. 6 is a circuit diagram of the example circuit. FIG. 6 shows that the resistors 503 are connected in parallel, but it will be appreciated that they could also be connected in series or in a combination of series and parallel connections. In an example, a direct current input voltage of twenty-four volts is applied across the resistors 503. The resistance values of the resistors 503 range from 3.3 kilohms to 6.8 kilohms in order to avoid localised areas generating more heat than surrounding regions. It will also be appreciated that the present invention is not limited to any particular input voltage or resistance values.

Thermal imaging or computer modelling software can be used to map the spatial heat distribution generated by the resistors 503 over the surface 52 of the substrate 500. Based upon the results of the thermal imaging or computer modelling, the value and/or position of individual resistors can be adjusted to achieve a desired heat distribution. Thus, the temperature at each point on the surface 52 of the substrate 500, and hence the temperature at each point on the surface of the pad assembly 30, can be optimised to achieve a desired therapeutic effect. For example, resistors 503 can be concentrated in the vicinity of the electrodes 514, in order that the temperature of the conducting areas 101 of the pad assembly 30 is greater than in the surrounding regions of the pad assembly; this can enhance the synergistic effects of heat therapy and electrical stimulation, whilst minimising the total amount of heat energy that is supplied to the body. Other heat distributions are also possible. The circuit 51 shown in FIG. 3 is designed to distribute heat substantially evenly over the surface 52 of the substrate 500.

As shown by the grey shaded regions in FIG. 3, the conductors 512a, 512b have a variable width and are shaped (via a patterning process) so that they comprise relatively wide regions of conducting material. This ensures that the conductors 512 have a low resistance relative to the resistances of each resistor 503; this ensures that the majority of the heat produced by the heating current is dissipated in the resistors 503 and that negligible heat is dissipated in the conductors 512. The use of relatively wide regions of conducting material allows heat dissipation in the conductors 512 to be disregarded when optimising the heat distribution over the surface of the substrate 500, such that the heat distribution can be treated as being determined solely by the resistance value and position of each resistor 503. This simplifies the process of designing the circuit 51 to produce a particular heat distribution.

The temperature sensor 510 is mounted on the second surface 52 of the substrate 500, using surface-mount technology. The temperature sensor 510 is preferably mounted at the point equidistant between the electrodes 514a, 514b. This is to give an indication of the temperature near the region where electrical stimulation is applied, although the temperature sensor 510 could be placed at any other suitable point on the second surface 52. The positive and negative supply voltages for the temperature sensor 510 are supplied by the pins labelled 'Temp+' and 'Temp−' respectively in the connector 507. The temperature sensor 510 is coupled to the connector 507 by the conductors 511 patterned on the first surface 53 of the substrate 500. Vias through the substrate 500 connect the conductors 511 on the first surface 53 to the temperature sensor 510 and connector 507 that are mounted on the second surface 52. The temperature sensor 510 can be a resistance thermometer or a thermocouple. The temperature sensor is preferably a platinum resistance thermometer (PRT), and is more preferably a Pt1000 element. A Pt1000 element is preferable due to its high accuracy. Resistance thermometers are known to those skilled in the art and need not be described in further detail.

As mentioned previously, the electrodes 514a, 514b are patterned on the first surface 53 of the substrate 500. The electrodes 514 comprise an electrically conducting material. Preferably the electrodes 514 are copper. Copper is preferable due to its high conductivity. The first surface 53 is mostly coated with an insulating plastic so as to cover the conductors 511, although the electrodes 514 are left exposed. Those of ordinary skill in the art will appreciate that the present invention is not limited to the materials of the current example. An electrical stimulation current is delivered from the console 20 to the electrodes 514a, 514b by the pins of the connector 507 labelled 'EM1' and 'EM2' respectively. The electrodes 514 are coupled to the connector 507 by the conductors 511 patterned on the first surface 53. Vias through the substrate 500 connect the conductors 511 on the first surface 53 to the connector 507 that is mounted on the second surface 52.

Thus, the circuit 51 described herein comprises a heating element 502 and one or more electrodes 514 that are provided on different surfaces 52, 53 of a substrate 500. Providing the heating element 502 and electrodes 514 on different surfaces of the substrate 500 is advantageous because it allows the layout of the heating element 502 to be independent of the layout of the electrodes 514 and their associated conductors 511. That is, the design of the heating element 502 can be modified to produce a particular heat distribution (as described in more detail above), without requiring any modification to the design of the electrodes 514. This simplifies the process of designing the circuit 51.

The use of a patterning process to form the electrodes 514 and the heating element 502 results in a pad assembly 30 that is compact and simple to manufacture. In particular, patterning eliminates the need for external components to secure the heating element 502 and electrodes 514.

As explained above, preferred examples of the circuit 51 comprise a plurality of surface-mounted components that are all mounted on the second surface 52 of the substrate 500. It is preferable that no components are mounted on the first surface 53 of the substrate 500. The absence of components on the first surface 53 is advantageous because it allows the electrodes 514a, 514b to abut, and make good electrical contact with, a respective conducting area 101a, 101b when the circuit 51 is installed in a pad assembly 30 (as shown in FIG. 2). Additionally, mounting components on only one surface of the substrate 500 simplifies manufacturing of the circuit 51.

Other electronic components could be mounted on the substrate 500 and, preferably, mounted on the second surface 52 of the substrate. For example, logic components such as a programmable logic device, microprocessor or microcontroller could be mounted on the substrate 500. Such logic components could be used to control the heat and/or electrical stimulation that is applied to a user. As another example, one or more sensors could be mounted on the substrate 500, in addition to the temperature sensor 510. As shown in FIG. 3, a visual indicator 505 can be mounted on the second surface 52 of the substrate 500. The visual indicator 505 is preferably a light emitting diode.

As mentioned previously, in use, the heating element 502 faces away from the skin of the user and the electrodes 514 face towards the skin. Thus, heat generated in the heating element 502 on the second surface 52 is conducted through the substrate 500 to the first surface 53, and is subsequently conducted to the body of a user through the casing body 100 of the pad assembly 30. This implies that the substrate 500 has a relatively high thermal conductivity in the direction between the second surface 52 and the first surface 53. This can be achieved by forming the substrate 500 from a relatively thin layer of material and/or by forming the substrate 500 from a material having a relatively high thermal conductivity.

Preferably the substrate 500 is flexible and so conforms to the contours of the body when the pad assembly 30 is placed on the body. Preferably the substrate 500 comprises plastics material and preferably the plastics material is chosen to allow the substrate 500 to be flexible. Examples of suitable materials include polyimide and polyether ether ketone (PEEK). Those skilled in the art will appreciate that the substrate 500 could comprise any other suitable material. Thus, the substrate 500, electronic components 502, 505, 507, 510, the conductors 511, 512 and the electrodes 514 collectively form a flexible circuit. Flexible circuit technology is defined by industry standards, such as IPC standards IPC-T-50, IPC-2223A and IPC-4202. Despite its flexibility, the substrate 500 is preferably substantially planar in the absence of an applied force.

It will be understood that the invention has been described above purely by way of example, and that modifications of detail can be made within the scope of the invention.

The invention claimed is:

1. A circuit for applying heat and electrical stimulation, the circuit comprising a substrate, the substrate comprising an electrode for applying electrical stimulation and a heating element, wherein at least one of the electrode and the heating element comprises an electrically conducting region patterned on a surface of the substrate wherein the substrate comprises a first surface and a second surface, the first surface being on a reverse side of the substrate with respect to the second surface, wherein the substrate is disposed between the electrode provided on the first surface and the heating element provided on the second surface.

2. The circuit of claim 1, wherein the position on the second surface of at least a portion of the heating element corresponds to the position on the first surface of the electrode, such that the at least a portion of the heating element is operable to heat the electrode.

3. The circuit of claim 2, wherein the heating element comprises one or more resistors, wherein the position of the one or more resistors on the second surface corresponds to the position on the first surface of the electrode.

4. The circuit of claim 1, wherein the heating element comprises one or more resistors mounted on a surface of the substrate.

5. The circuit of claim 1, wherein the heating element comprises a plurality of resistors, and wherein the resistors are positioned so as to produce a predetermined heat distribution when a current is applied to the heating element.

6. The circuit of claim 1, wherein the heating element comprises a plurality of resistors, each resistor having a respective resistance value, wherein the resistance values of the plurality of resistors are chosen so as to produce a predetermined heat distribution when a current is applied to the heating element.

7. The circuit of claim 1, wherein the heating element comprises one or more resistors, the one or more resistors being electrically connected to an electrically conducting region patterned on a surface of the substrate that forms part of the heating element.

8. The circuit of claim 7, wherein the electrically conducting region that forms part of the heating element is shaped such that its resistance is negligible relative to the resistance of each resistor.

9. The circuit of claim 1, wherein both the electrode and the heating element comprise an electrically conducting region patterned on a surface of the substrate.

10. The circuit of claim 1, wherein a temperature sensor is mounted on a surface of the substrate.

11. The circuit of claim 10, wherein the heating element comprises one or more resistors mounted on the same surface of the substrate as the temperature sensor.

12. The circuit of claim 10, wherein the circuit comprises a further electrode for applying electrical stimulation, and wherein the temperature sensor is positioned between the electrode and the further electrode.

13. The circuit of claim 1, wherein the substrate is flexible.

14. A circuit for applying heat and electrical stimulation, the circuit comprising an electrode for applying electrical stimulation and a heating element, wherein the circuit is formed on a flexible substrate, wherein the flexible substrate comprises a first surface and a second surface, the first surface being on a reverse side of the flexible substrate with respect to the second surface, wherein the flexible substrate is disposed between the electrode provided on the first surface and the heating element provided on the second surface.

15. The circuit of claim 14, wherein the position on the second surface of at least a portion of the heating element corresponds to the position on the first surface of the electrode, such that the at least a portion of the heating element is operable to heat the electrode.

16. The circuit of claim 15, wherein the heating element comprises one or more resistors, wherein the position of the one or more resistors on the second surface corresponds to the position on the first surface of the electrode.

17. The circuit of claim 14, wherein the heating element comprises one or more resistors mounted on a surface of the flexible substrate.

18. The circuit of claim 14, wherein the heating element comprises a plurality of resistors, and wherein the resistors are positioned so as to produce a predetermined heat distribution when a current is applied to the heating element.

19. The circuit of claim 14, wherein the heating element comprises a plurality of resistors, each resistor having a respective resistance value, wherein the resistance values of the plurality of resistors are chosen so as to produce a predetermined heat distribution when a current is applied to the heating element.

20. The circuit of claim 14, wherein the heating element comprises one or more resistors, the one or more resistors being electrically connected to an electrically conducting region that forms part of the heating element, wherein the electrically conducting region is shaped such that its resistance is negligible relative to the resistance of each resistor.

21. The circuit of claim 14, wherein a temperature sensor is mounted on a surface of the flexible substrate.

22. The circuit of claim 21, wherein the heating element comprises one or more resistors mounted on the same surface of the flexible substrate as the temperature sensor.

23. The circuit of claim 21, wherein the circuit comprises a further electrode for applying electrical stimulation, and wherein the temperature sensor is positioned between the electrode and the further electrode.

\* \* \* \* \*